United States Patent
Geiculescu et al.

(10) Patent No.: US 8,394,539 B2
(45) Date of Patent: Mar. 12, 2013

(54) LITHIUM SALTS OF FLUORINATED BORATE ESTERS FOR LITHIUM-ION BATTERIES

(75) Inventors: Olt E. Geiculescu, Easley, SC (US); Ion C. Halalay, Grosse Pointe Park, MI (US); Darryl D. Desmarteau, Seneca, SC (US); Stephen E. Creager, Clemson, SC (US)

(73) Assignee: GM Global Technology Operations LLC, Detroit, MI (US)

(*) Notice: Subject to any disclaimer, the term of this patent is extended or adjusted under 35 U.S.C. 154(b) by 0 days.

(21) Appl. No.: 13/528,899

(22) Filed: Jun. 21, 2012

(65) Prior Publication Data
US 2012/0328938 A1  Dec. 27, 2012

Related U.S. Application Data

(60) Provisional application No. 61/500,849, filed on Jun. 24, 2011.

(51) Int. Cl.
- *H01M 10/40* (2006.01)
- *H01M 6/14* (2006.01)
- *H01M 6/18* (2006.01)
- *C07F 5/02* (2006.01)
- *C01B 35/06* (2006.01)

(52) U.S. Cl. ........ 429/300; 429/188; 429/200; 429/303; 429/307; 429/321; 562/7; 423/3; 568/6

(58) Field of Classification Search ............... 429/200, 429/300–347, 188; 562/7; 423/293; 568/6
See application file for complete search history.

(56) References Cited

U.S. PATENT DOCUMENTS

2008/0226989 A1* 9/2008 Angell et al. ............ 429/300
2011/0111308 A1  5/2011 Halalay et al.

OTHER PUBLICATIONS

J. Barthel et al.; A New Class of Electrochemically and Thermally Stable Lithium Salts for Lithium Battery Electrolytes; I. Synthesis and Properties of Lithium bis[1,2-benzenediolato(2-)-O,O']borate; J. Electrochem. Soc., vol. 142, No. 8, Aug. 1995; The Electrochemical Society, Inc.; pp. 2527-2531.
J. Barthel et al.; A New Class of Electrochemically and Thermally Stable Lithium Salts for Lithium Battery Electrolytes; II. Conductivity of Lithium Organoborates in Dimethoxyethane and Propylene Carbonate; J. Electrochem. Soc., vol. 143, No. 11, Nov. 1996; The Electrochemical Society, Inc.; pp. 3565-3571.
J. Barthel et al.; A New Class of Electrochemically and Thermally Stable Lithium Salts for Lithium Battery Electrolytes; III. Synthesis and Properties of Some Lithium Organoborates; J. Electrochem. Soc., vol. 143, No. 11, Nov. 1996; The Electrochemical Society, Inc.; pp. 3572-3575.
J. Barthel et al.; A New Class of Electrochemically and Thermally Stable Lithium Salts for Lithium Battery Electrolytes; IV. Investigations of the Electrochemical Oxidation of Lithium Organoborates; J. Electrochem. Soc., vol. 144, No. 11, Nov. 1997; The Electrochemical Society, Inc.; pp. 3866-3870.

(Continued)

*Primary Examiner* — Milton I Cano
*Assistant Examiner* — Ling R Zeng
(74) *Attorney, Agent, or Firm* — Reising Ethington P.C.

(57) ABSTRACT

Lithium salts with fluorinated chelated orthoborate anions are prepared and used as electrolytes or electrolyte additives in lithium-ion batteries. The lithium salts have two chelate rings formed by the coordination of two bidentate ligands to a single boron atom. In addition, each chelate ring has two oxygen atoms bonded to one boron atom, methylene groups bonded to the two oxygen atoms, and one or more fluorinated carbon atoms bonded to and forming a cyclic bridge between the methylene groups.

13 Claims, 9 Drawing Sheets

OTHER PUBLICATIONS

J. Barthel et al.; A New Class of Electrochemically and Thermally Stable Lithium Salts for Lithium Battery Electrolytes; V. Synthesis and Properties of Lithium Bis[2,3-pyridinediolato(2-)-O,O']borate; Journal of The Electrochemical Society, 147(1) 21-24 (2000); The Electrochemical Society, Inc.; pp. 21-24.

Wu Xu et al.; A Fusible Orthoborate Lithium Salt with High Conductivity in Solutions; Department of Chemistry, Arizona State University, Tempe, Arizona 85287-1604, USA; Electrochemical and Solid-State Letters, 3 (8) 366-368 (2000).

* cited by examiner

LITHIUM SALTS OF FLUORINATED BORATE ESTERS FOR LITHIUM-ION BATTERIES

This application claims the benefit of U.S. Provisional Application No. 61/500,849, titled "Lithium Salts of Fluorinated Boron Esters for Lithium-Ion Batteries" and filed Jun. 24, 2011, the contents of which are incorporated herein by reference.

TECHNICAL FIELD

This invention provides new lithium salts with fluorinated chelated orthoborate anions for use as electrolyte materials in secondary lithium-ion batteries. As specific examples, this invention pertains to the synthesis and characterization of lithium bis(2,2,3,3-tetrafluoro-1,4-butanediol)-borate ester and lithium bis(2,2,3,3,4,4-hexafluoro-1,5-pentanediol)-borate ester as such lithium salts.

BACKGROUND OF THE INVENTION

Secondary lithium-ion batteries can be made to provide high energy from a relatively low mass of material. During discharge, lithium ions are formed in a negative electrode material and flow from the negative electrode through an electrolyte medium to a lithium-ion-receiving positive electrode material. This flow of lithium ions provides a corresponding flow of electrons from the negative electrode through an external circuit and an external power-consuming device(s) to the positive electrode in order to power the external device. When the lithium ion content in the negative electrode is sufficiently depleted such that the battery is considered discharged, an external voltage may be applied to the cell to reverse the direction of lithium ion flow. During recharge, the lithium ions flow from the positive electrode, through the electrolyte medium and back to the negative electrode where the ions are reduced to elemental lithium.

Electrolytes of lithium-ion batteries typically comprise one or more lithium salts dissolved in suitable organic solvents or ionic liquids that are substantially free of water. The lithium salts dissociate into lithium ions in the electrolyte solutions and are transported therethrough between the positive and negative electrodes of the battery cells during discharge and recharge.

Suitable electrolytes for lithium-ion batteries should have good ionic conductivity and be capable of conducting lithium ions over the temperature range at which the batteries are expected to operate. The lithium salts should also be sufficiently soluble in commonly used solvents and ionic liquids of lithium-ion batteries. Further, the electrolytes should be thermally stable and chemically compatible with the positive electrode and negative electrode materials.

Numerous attempts have been made to provide electrolytes with a balanced combination of these desirable properties. However, there remains a need for an electrolyte that can effectively function in the thermally, chemically, and electrochemically demanding environment of lithium-ion batteries.

SUMMARY OF THE INVENTION

Two new lithium salts with fluorinated chelated orthoborate anions have been prepared and found to be useful as electrolytes or electrolyte additives in lithium-ion batteries. The lithium salts are: (A) lithium bis(2,2,3,3-tetrafluoro-1,4-butanediol)-borate ester (LiBFBDB) and (B) lithium bis(2,2,3,3,4,4-hexafluoro-1,5-pentanediol)-borate ester (LiBHFPDB).

Each of these lithium salts has two chelate rings formed by the coordination of two bidentate ligands to a single boron atom. Each chelate ring consists of a pair of oxygen atoms covalently bonded to the boron atom, with four or five carbon atoms forming a cyclic bridge between the pair of oxygen atoms. The first and last carbons of each bridge are methylene groups ($-CH_2-$ groups), but the remaining carbon atoms each bond to two fluorine atoms ($-CF_2-$ groups). And, it is believed that the $-CH_2-$ bridges between the oxygen atoms and the perfluorinated portion of each chelate ring are responsible for the exceptional thermal and hydrolytic stability of these two lithium salts.

Accordingly, embodiments of the present invention are directed to lithium borate salts with similar chelate ring structures. These lithium salts include a lithium cation and an anion of a borate ester chelate complex having two bidentate ligands coordinated to a single boron atom through two oxygen atoms. Each chelate ring of the borate anion is characterized by the presence of two oxygen atoms bonded to one boron atom, methylene groups bonded to the two oxygen atoms, and one or more fluorinated carbon atoms bonded to and forming a cyclic bridge between the methylene groups.

In preferred embodiments, the bidentate ligands are partially fluorinated diols with the general formula $HO-CH_2-R-CH_2-OH$, where R comprises one or more fluorinated carbons ($-CF_2-$ groups). For example, the bidentate ligands may comprise fluorinated derivatives of 1,4-butanediol or 1,5-pentanediol. Other fluorinated diols may be used, so long as two methylene groups are adjacent to the hydroxyl groups ($-OH$ groups) of each diol, and the remaining carbon atoms in the chain are fluorinated.

The lithium borate salts may be synthesized by forming a particular mixture of boric acid ($H_3BO_3$), lithium hydroxide (LiOH), and a suitably fluorinated diol, followed by heating and calcining the mixture. For example, solid particles of LiBFBDB may be synthesized from a finely ground mixture of boric acid ($H_3BO_3$), lithium hydroxide (LiOH) and 2,2,3,3-tetrafluoro-1,4-butane-diol (TFBD). The particulate mixture is suitably heated to a temperature of about 110° C. for about 24 hours in air. Then, the mixture is calcined overnight under dynamic vacuum at a temperature of about 80° C. to produce particles of LiBFBDB salt. As another example, solid particles of LiBHFPDB may be synthesized from a finely ground mixture of boric acid ($H_3BO_3$), lithium hydroxide (LiOH) and 2,2,3,3,4,4-hexafluoro-1,5-propanediol (HFPD). The particulate mixture is heated to a temperature of about 110° C. for about 24 hours in air. Then, the mixture is calcined overnight under dynamic vacuum at a temperature of about 80° C. to produce particles of LiBHFPDB salt.

In practice, solid particles of the lithium borate salts are dissolved in non-aqueous organic solvents or ionic liquids (ILs) to produce electrolyte solutions having electrolyte concentrations of less than one mole per liter. At such concentrations, these electrolyte solutions exhibit suitable conductivity and viscosity for lithium-ion battery applications. In addition, these electrolyte solutions are electrochemically and thermally stable, and are not susceptible to hydrolysis.

Suitable non-aqueous organic solvents include organic carbonates, organic esters, organic ethers, sulfur-containing solvents, aprotic solvents, and partially fluorinated derivatives of these organic solvents, as well as mixtures thereof. For example, solids particles of the lithium borate salts may be dissolved in ethylene carbonate (EC), propylene carbonate (PC), butylene carbonate (BC), dimethyl carbonate (DMC), diethyl carbonate (DEC), ethyl methyl carbonate (EMC), and methyl propyl carbonate (MPC), as well as mixtures thereof to produce electrolyte solutions suitable for lithium-ion battery applications.

Suitable ionic liquids for dissolving solids particles of the lithium borate salts include 1-ethyl-3-methyl-imidazolium bis(fluorosulfonyl)imide ($EMIM^+/FSI^-$), 1-ethyl-3-methyl-imidazolium bis(trifluoromethylsulfonyl)imide ($EMIM^+/TFSI^-$), N-methyl-N-butyl-pyrrolidinium bis(fluorosulfonyl)imide ($Py_{14}^+/FSI^-$), and N-methyl-N-propyl-piperidinium bis(fluorosulfonyl)imide ($PP_{13}^+/FSI^-$).

The as-synthesized lithium borate salts may be used alone or in combination with other lithium salts in the electrolyte solutions of lithium-ion batteries. Suitable lithium salts for use in combination with LiBFBDB and/or LiBHFPDB include lithium hexafluorophosphate ($LiPF_6$), lithium bis(oxalato)borate (LiBOB), lithium bis(1,1,1,4,4,4-hexafluoro-2,3-bis(trifluoromethyl) butane-2,3-diol)-borate ester (LiHFBTMB), lithium fluoroalkylphosphate (LiFAP), lithium hexafluoroarsenate monohydrate ($LiAsF_6$), lithium perchlorate ($LiClO_4$), lithium tetrafluoroborate ($LiBF_4$), and/or lithium trifluoromethanesulfonate ($LiCF_3SO_3$).

The lithium borate salts may be used in combination with a variety of negative and positive electrode materials of lithium-ion batteries. For example, the as-synthesized LiBFBDB and LiBHFPDB salts may be used in combination with negative electrodes containing lithium (Li), titanium (Ti), silicon (Si), tin (Sn), alloys of Li, Ti, Si, and/or Sn, or a carbonaceous material, such as a composite of carbon (C) with silicon (Si) and tin (Sn). Suitable positive electrode materials may comprise one or more transition metal oxides, metal phosphates, metal silicates, lithium iron phosphates, or metal sulfides.

Other objects and advantages of the invention will be apparent from further description and illustration of preferred embodiments which follows in this specification. In this description, reference is had to drawing figures which are described in the next section of this specification.

DESCRIPTION OF PREFERRED EMBODIMENTS

Figure 1:
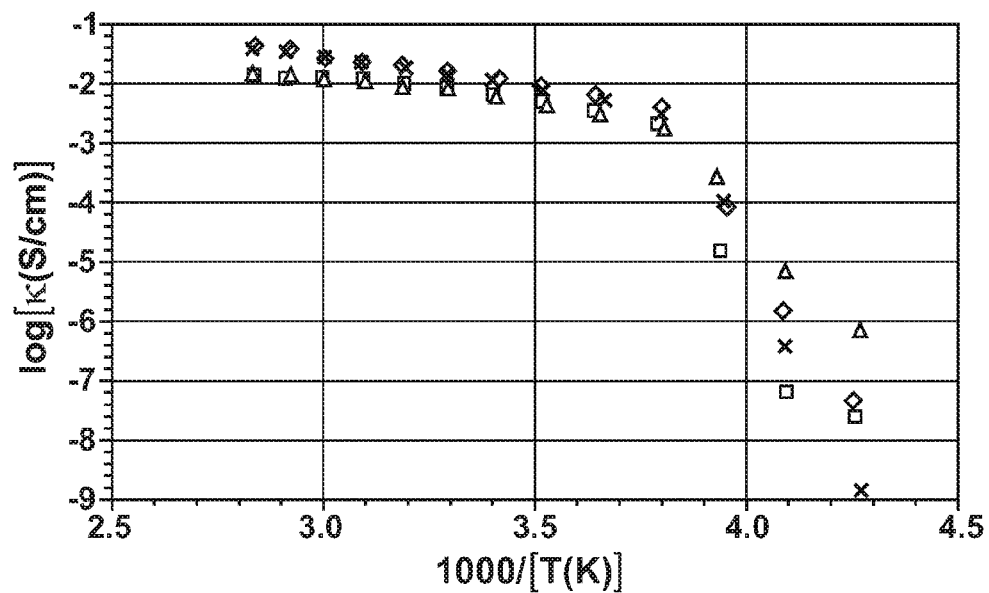
FIG. 1 is an Arrhenius plot of Ionic Conductivity (log [κ(S/cm)]) vs. 1000/T(K) and shows the ionic conductivity of four 0.3M electrolyte solutions over the temperature range of −40 to +80° C. Solid particles of the two new lithium salts and two known lithium salts were dissolved in an ionic liquid of $EMIM^+/FSI^-$ to form the four 0.3M electrolyte solutions. Data points for 0.3M electrolyte solutions of LiBFBDB, LiBHFPDB, LiHFBTMB, and LiBOB are depicted as squares, Xs, diamonds, and triangles, respectively.

Lithium salts with fluorinated chelated orthoborate anions may be prepared and used as electrolytes or electrolyte additives in electrochemical cells of lithium-ion batteries to improve certain desirable characteristics of the batteries.

Two exemplary lithium salts are: (A) lithium bis(2,2,3,3-tetrafluoro-1,4-butanediol)borate ester (LiBFBDB) and (B) lithium bis(2,2,3,3,4,4-hexafluoro-1,5-pentanediol)borate ester (LiBHFPDB), which have the following chemical structures:

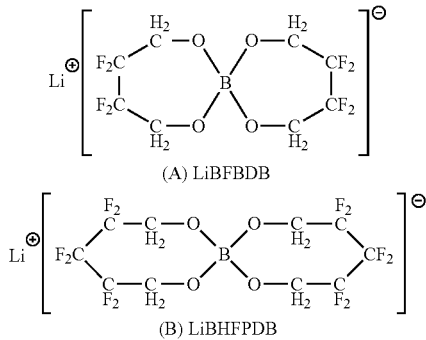

(A) LiBFBDB (B) LiBHFPDB

These specific compounds are found to provide excellent properties as additives to electrolyte mixtures in lithium ion battery cells. As will be discussed further in this specification, analogues of these lithium borate ester salts may additionally or alternatively be used as electrolytes or electrolyte additives in electrochemical cells of lithium-ion batteries.

As shown in the above schematic structural formulas, each of these lithium salts includes a lithium cation and a chelated borate ester anion with two chelate rings. Each chelate ring consists of a pair of oxygen atoms bonded to a single boron atom, with either four or five carbon atoms forming a bridge between the two oxygen atoms. The first and last carbons of each bridge are methylene groups (—CH$_2$— groups), and the two or three intermediate carbon atoms are fluorinated (—CF$_2$— groups). In these exemplary lithium salts, the bidentate chelating ligands are (A) 2,2,3,3-tetrafluoro-1,4-butanediol and (B) 2,2,3,3,4,4-hexafluoro-1,5-pentanediol.

Particles of LiBFBDB may be prepared from a particulate mixture of boric acid (H$_3$BO$_3$), lithium hydroxide (LiOH), and 2,2,3,3-tetrafluoro-1,4-butane-diol, as shown by Reaction 1 below. In the examples below, solid particles of LiBF-BDB were synthesized by mixing 1.237 g (20.0 mmol) of 100% pure boric acid (H$_3$BO$_3$) with 0.488 g (20.0 mmol) of 98% pure lithium hydroxide (LiOH) and 6.616 g (40.0 mmol) of 98% pure 2,2,3,3-tetrafluoro-1,4-butane diol. The prepared mixture may then be ground together and heated at 110° C. for 24 hours in air. The obtained crude product may be heated overnight under dynamic vacuum at 80° C. to produce approximately 5.32 grams (15.7 mmol) of LiBFBDB (yield of 78.5%).

Reaction 1:

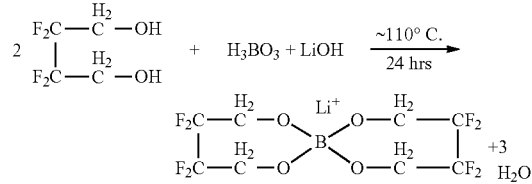

Particles of LiBHFPDB may be prepared from a particulate mixture of boric acid (H$_3$BO$_3$), lithium hydroxide (LiOH), and 2,2,3,3,4,4-hexafluoro-1,5-pentane diol, as shown by Reaction 2 below. In the following examples, solid particles of LiBHFPDB were synthesized by mixing 0.618 g (10.0 mmol) of 100% pure boric acid (H$_3$BO$_3$) with 0.244 g (10.0 mmol) of 98% pure lithium hydroxide (LiOH) and 4.328 g (20.0 mmol) of 98% pure 2,2,3,3,4,4-hexafluoro-1,5-pentane diol. The prepared mixture may be ground together and heated in open air at 110° C. for about 24 hours. The obtained crude product may then be heated overnight at a temperature of about 80° C. under dynamic vacuum to produce approximately 3.28 grams (7.5 mmol) of LiBHFPDB (yield 75%).

Reaction 2:

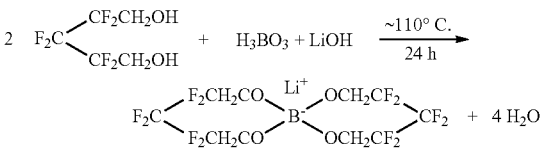

For comparison, particles of lithium bis(hexafluoro-2,3-bis(trifluoromethyl)butane-2,3-diol)borate ester (LiHF-BTMB) were synthesized by mixing together and grinding solid particles of boric acid, H$_3$BO$_3$ (0.556 g, 9.0 mmol) and lithium hydroxide, LiOH (98%, 0.220 g, 9.0 mmol). The solid particles were then transferred to a 50 mL flask and liquid hexafluoro-2,3-bis(trifluoromethyl)butane-2,3-diol (6.00 g, 18.0 mmol) is added to form a mixture. The mixture was heated in the flask to a temperature in the range of about 100° C. to 110° C. under nitrogen (N$_2$) gas for about 8 hours with a condenser on top of the flask. Thereafter, the mixture was further heated overnight at a temperature of about 100° C. in air. The obtained crude product was heated to a temperature of about 100° C. under dynamic vacuum for about 8 hours to produce approximately 4.40 g (6.45 mmol) of LiHFBTMB (yield 71.7%).

Particles of lithium bis(oxalato)borate (LiBOB) were also prepared for comparison. LiBOB is another proposed salt for use in electrolytes of lithium-ion batteries; however, LiBOB has limited solubility in linear carbonates and forms highly viscous electrolyte solutions. In addition, LiBOB is thermally and hydrolytically unstable.

The electrochemical and thermodynamic properties of LiBFBDB and LiBHFPDB were evaluated to determine their potential for use as electrolytes or electrolyte additives in lithium-ion batteries. For comparison, the electrochemical and thermodynamic properties of LiHFBTMB and LiBOB were similarly evaluated. There is particular interest, for example, in evaluating LiBFBDB and LiBHFPDB for use as additives in lithium-ion batteries with high-voltage cathode materials such as nickel-cobalt-manganese oxide and nickel-manganese oxide spinel compositions. Such electrode compositions can be intercalated with lithium ions and are known to display a 4.6 to 5 volt potential in combination with a lithium-intercalated graphite anode. In addition, there is interest in determining how additions of small portions of the LiBFBDB and LiBHFPDB resist hydrolysis and how they affect the conductivity of, for example, a $LiPF_6$-based electrolyte.

Suitable amounts of each of LiBFBDB, LiBHFPDB, LiHFBTMB, and LiBOB particles were added both to water at room temperature (30° C.) and to water at 60° C. with stirring for 2 hours. $^{11}B$ NMR spectroscopy indicated that about sixty-five percent of the LiBOB compounds dissolved in water had decomposed after two hours of exposure at room temperature, and, after two hours, the LiBOB compounds had completely decomposed in the 60° C. water. However, the new lithium salts of LiBFBDB and LiBHFPDB did not appear to experience any decomposition during exposure to water at either temperature. LiHFBTMB, exhibited only partial decomposition both at room temperature (10%) and at 60° C. (18%).

A common electrolyte composition used in lithium-ion batteries of automotive vehicles comprises a mixture of 1M $LiPF_6$ dissolved in equal parts by volume of ethylene carbonate (EC) and dimethyl carbonate (DMC). This representative electrolyte solution was prepared for comparison with electrolyte compositions containing small amounts of LiBFBDB or LiBHFPDB in a binary solvent of EC:DMC.

The electrical conductivity of the representative 1M $LiPF_6$ electrolyte solution in EC:DMC (1:1) at 25° C. was 10.36 mS $cm^{-1}$. Two modified samples of the representative 1M $LiPF_6$ electrolyte solution were prepared in which LiBFBDB, in amounts of 0.5% and 1% by weight, based on the $LiPF_6$ content, were stirred into and dissolved in the mixed carbonates solvent. The electrical conductivity values of these modified samples were 10.46 mS $cm^{-1}$ and 10.33 mS $cm^{-1}$, respectively. Two additional modified samples of the representative 1M $LiPF_6$ electrolyte solution were prepared in which LiBHFPDB, also in amounts of 0.5% and 1% by weight, based on the $LiPF_6$ content, were stirred into and dissolved in the mixed carbonates solvent. The electrical conductivity values of these modified samples were both 10.38 mS $cm^{-1}$. Thus, the addition of small amounts of LiBFBDB or LiBHFPDB to a 1M $LiPF_6$ electrolyte solution in EC:DMC (1:1) does not significantly affect the electrical conductivity of the solution.

In further testing, it was demonstrated that additions of about one-percent by weight of LiBFBDB or LiBHFPDB to an $LiPF_6$-containing electrolyte solution provided suitable thin coating layers of solid electrode interface material on the electrodes of lithium ion cells for enhanced electrochemical performance of the cells. This was accomplished without adversely affecting the electrochemical stability of the cells or significant reduction in the capacity of the cell during prolonged cycling. The cycle life of the cells in which the LiBFBDB or LiBHFPDB compounds were used was not shortened even when they were used in higher potential cells.

It was also desired to evaluate the performance of the LiBFBDB and LiBHFPDB compounds in ionic liquids contemplated for use in lithium-ion batteries. Suitable amounts of LiBFBDB, LiBHFPDB, LiHFBTMB, and LiBOB were dissolved in ionic liquids (ILs) in order to evaluate their electrochemical and thermodynamic properties. Specifically, 0.3 and 0.6 molar electrolyte solutions of LiBFBDB, LiBHFPDB, LiHFBTMB, and LiBOB were prepared by dissolving suitable amounts of the lithium salts the ionic liquids of $EMIM^+/FSI^-$, $EMIM^+/TFSI^-$, $Py_{14}^+/FSI^-$ and $PP_{13}^+/FSI^-$.

The purity of the ionic liquids and the as-prepared electrolyte solutions was tested using $^1H$, $^7Li$ and $^{19}F$ nuclear resonance spectroscopy (NMR). The ionic conductivities of the solutions were measured by electrochemical impedance spectroscopy (EIS) in a two irreversible Ni electrode cell configuration using a Solartron SI 1260 frequency response analyzer (FRC) connected to an electrochemical interface Solartron SI 1287. The thermal properties (melting point, $T_m$, crystallization point, $T_c$ and glass transition temperature $T_g$) of the solutions were determined by differential scanning calorimetry (DSC) at temperatures between −80 and +100° C. or −120 and +100° C. with a temperature gradient of 10° C. per minute using a TA Instrument.

The intrinsic ionic conductivities of the ionic liquids were evaluated. The ionic conductivities of the aromatic $EMIM^+/TFSI^-$ and $EMIM^+/FSI^-$ solvents appear relatively constant, but fall abruptly at temperatures below −10° C. due, most probably, to their solidifying (freezing). The ionic conductivities of the $Py_{14}^+/FSI^-$ and $PP_{13}^+/FSI^-$ solvents exhibit a monotonic decrease over the entire temperature range of +80 to −40° C. due to the absence of any phase transitions.

FIG. 1 shows the ionic conductivities of the as-synthesized electrolyte solutions using a solvent of $EMIM^+/FSI^-$ from −40 to +80° C. The 0.3M LiBOB, LiBFBDB, LiHFBTMB and LiBHFPDB-containing solutions all exhibited good ionic conductivity in the temperature range of +80 to −10° C. But, at temperatures below −10° C., the ionic conductivities of the solutions drops abruptly, which is likely due to freezing of the ionic liquids.

Figure 2:
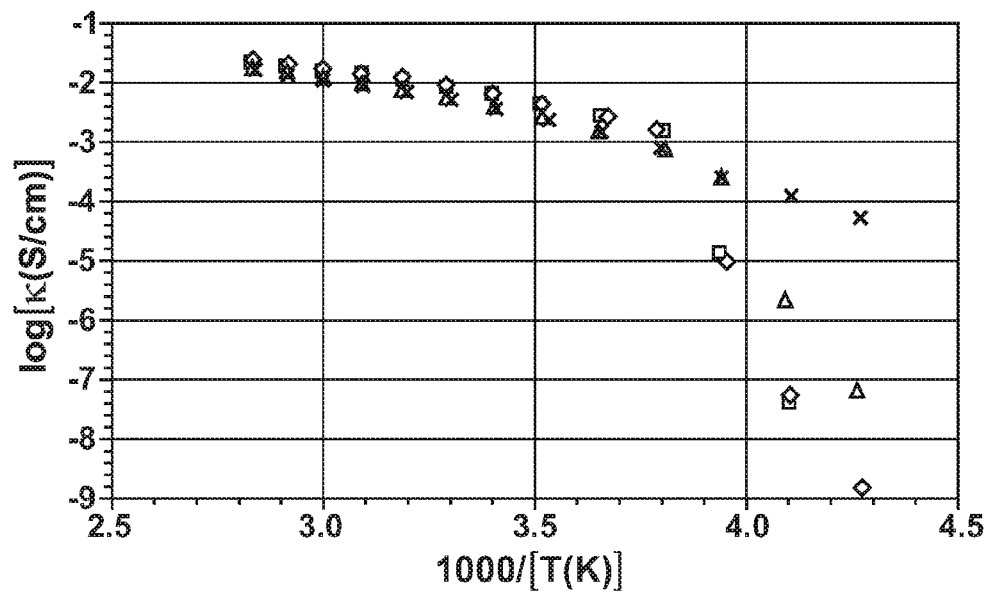
FIG. 2 is an Arrhenius plot of Ionic Conductivity (log [κ(S/cm)]) vs. 1000/T(K) and shows the ionic conductivity of four 0.3M electrolyte solutions over the temperature range of −40 to +80° C. Solid particles of the two new lithium salts and two known lithium salts were dissolved in an ionic liquid of $EMIM^+/TFSI^-$ to form the four 0.3M electrolyte solutions. Data points for 0.3M electrolyte solutions of LiBFBDB, LiBHFPDB, LiHFBTMB, and LiBOB are depicted as squares, Xs, diamonds, and triangles, respectively.

FIG. 2 shows the ionic conductivities of the as-synthesized electrolyte solutions using a solvent of $EMIM^+/TFSI^-$. The ionic conductivities of these 0.3M solutions appear to be lower than the conductivities observed for the $EMIM^+/FSI^-$-based electrolytes. As before, the ionic conductivities for all three solutions fell steeply after about −10° C., which is also likely due to the phase change of the ionic liquid.

Figure 3:
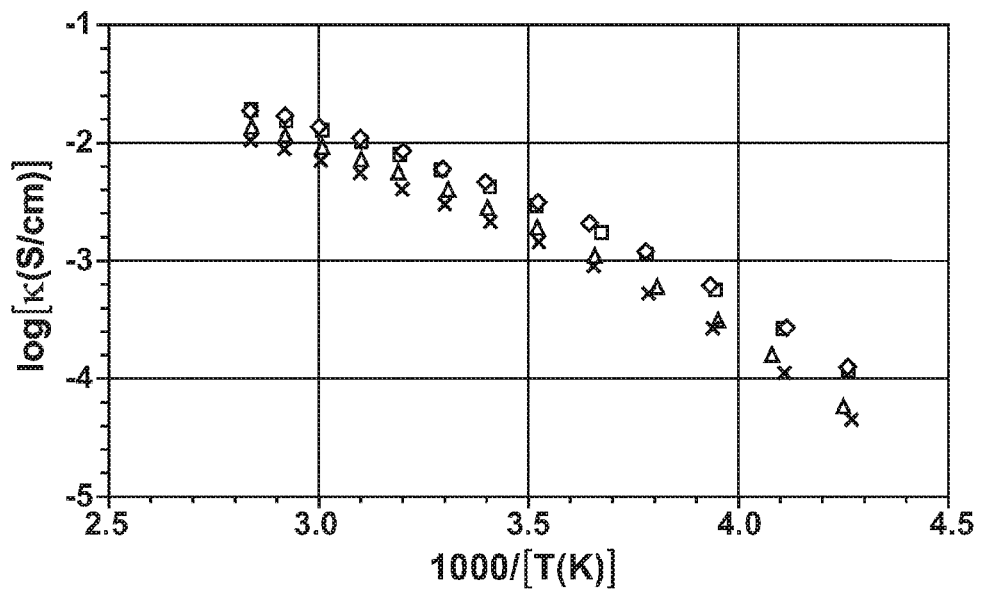
FIG. 3 is an Arrhenius plot of Ionic Conductivity (log [κ(S/cm)]) vs. 1000/T(K) and shows the ionic conductivity of four 0.3M electrolyte solutions over the temperature range of −40 to +80° C. Solid particles of the two new lithium salts and two known lithium salts were dissolved in an ionic liquid of $Py_{14}^+/FSI^-$ to form the four 0.3M electrolyte solutions. Data points for 0.3M electrolyte solutions of LiBFBDB, LiBHFPDB, LiHFBTMB, and LiBOB are depicted as squares, Xs, diamonds, and triangles, respectively.
Figure 8:
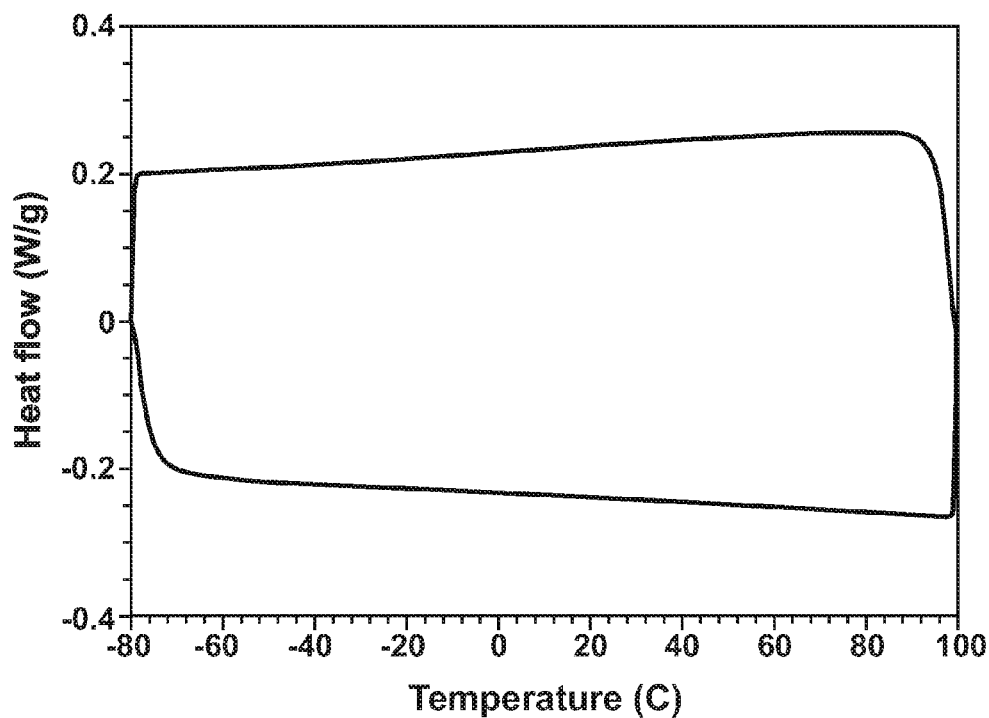
FIG. 8 is a plot of Heat Flow (W/g) vs. Temperature (° C.) and shows a thermogram for a 0.3M electrolyte solution of LiBFBDB in $Py_{14}^+/FSI^-$. Heat flow measurements were taken using DSC over the temperature range of −80 to +100° C. at a heating and cooling rate of 10° C. per minute.
Figure 12:
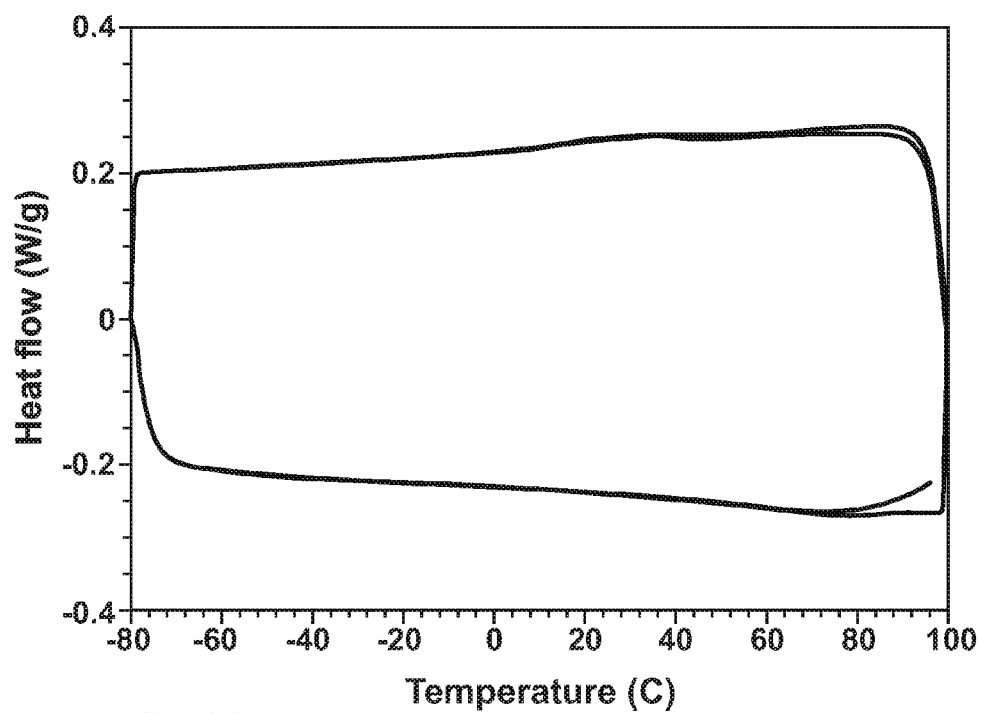
FIG. 12 is a plot of Heat Flow (W/g) vs. Temperature (° C.) and shows a thermogram for a 0.3M electrolyte solution of LiHFBTMB in $Py_{14}^+/FSI^-$. Heat flow measurements were taken using DSC over the temperature range of −80 to +100° C. at a heating and cooling rate of 10° C. per minute.
Figure 16:
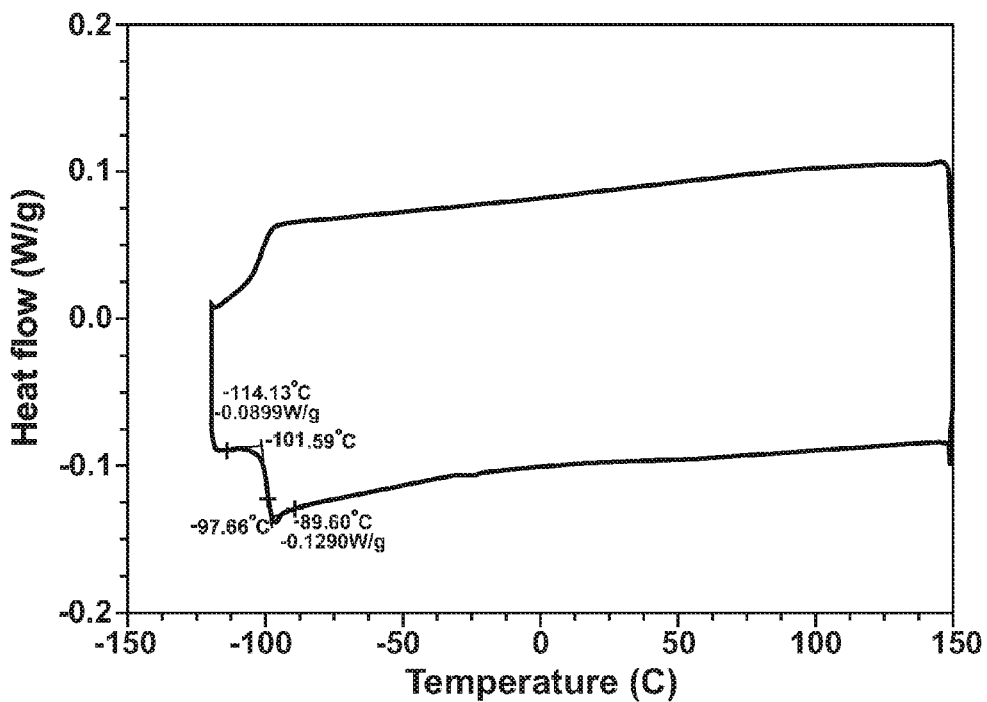
FIG. 16 is a plot of Heat Flow (W/g) vs. Temperature (° C.) and shows a thermogram for a 0.3M electrolyte solution of LiBHFPDB in Py$_{14}$$^+$/FSI$^-$. Heat flow measurements were taken using DSC over the temperature range of −120 to +100° C. at a heating and cooling rate of 10° C. per minute.
Figure 17:
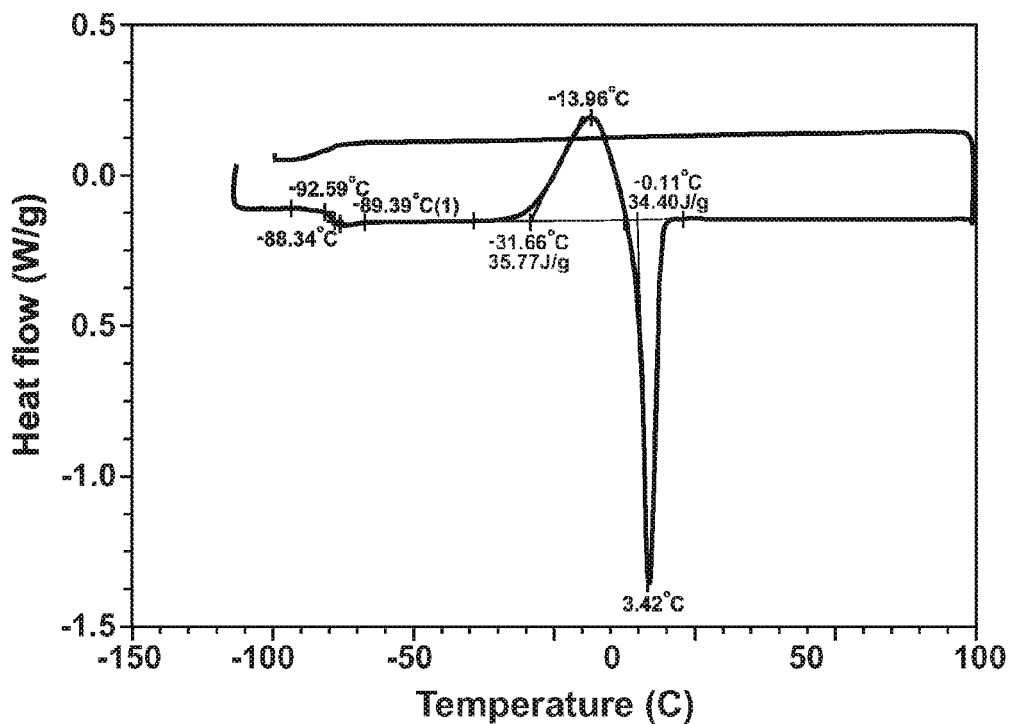
FIG. 17 is a plot of Heat Flow (W/g) vs. Temperature (° C.) and shows a thermogram for a 0.3M electrolyte solution of LiBHFPDB in PP$_{13}$$^+$/FSI$^-$ during a second heat and cool cycle. Heat flow measurements were taken using DSC over the temperature range of −120 to +100° C. at a heating and cooling rate of 10° C. per minute.

FIG. 3 shows the ionic conductivities of the as-synthesized 0.3M electrolyte solutions using a solvent of $Py_{14}^+/FSI^-$. When $Py_{14}^+/FSI^-$ is used as the solvent, there does not appear to be an abrupt decrease in the ionic conductivities of the solutions, which signals that this ionic liquid does not undergo any phase transitions in the temperature range studied. Also, the corresponding thermograms, shown in FIG. 8 for 0.3M LiBFBDB, FIG. 12 for 0.3M LiHFBTMB and FIG. 16 for 0.3M LiBHFPDB electrolyte solutions, are smooth and do not contain any peaks or troughs over the entire temperature range studied.

Additionally, the 0.3M LiBFBDB solution and the 0.3M LiBOB solution produce the highest ionic conductivity values. But, it is found that the LiBFBDB salt does not have all the disadvantages that LiBOB has, and is easily synthesized from the starting materials. Accordingly, LiBFBDB salt has potential for use in electrolytes or as an electrolyte additive in lithium-ion batteries.

Figure 4:
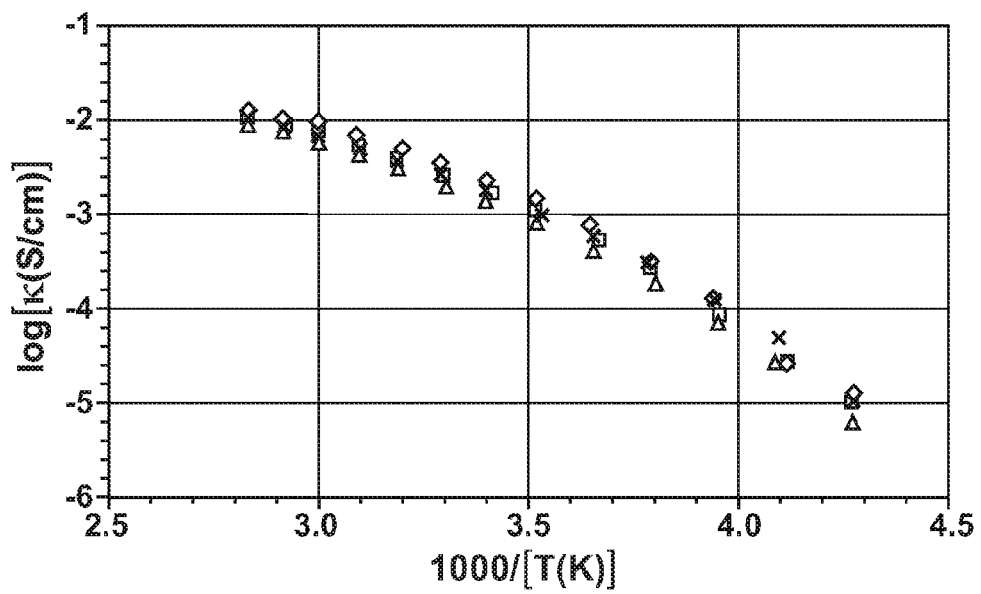
FIG. 4 is an Arrhenius plot of Ionic Conductivity (log [κ(S/cm)]) vs. 1000/T(K) and shows the ionic conductivity of four 0.3M electrolyte solutions over the temperature range of −40 to +80° C. Solid particles of the two new lithium salts and two known lithium salts were dissolved in an ionic liquid of $PP_{13}^+/FSI^-$ to form the four 0.3M electrolyte solutions. Data points for 0.3M electrolyte solutions of LiBFBDB, LiBHFPDB, LiHFBTMB, and LiBOB are depicted as squares, Xs, diamonds, and triangles, respectively.
Figure 9:
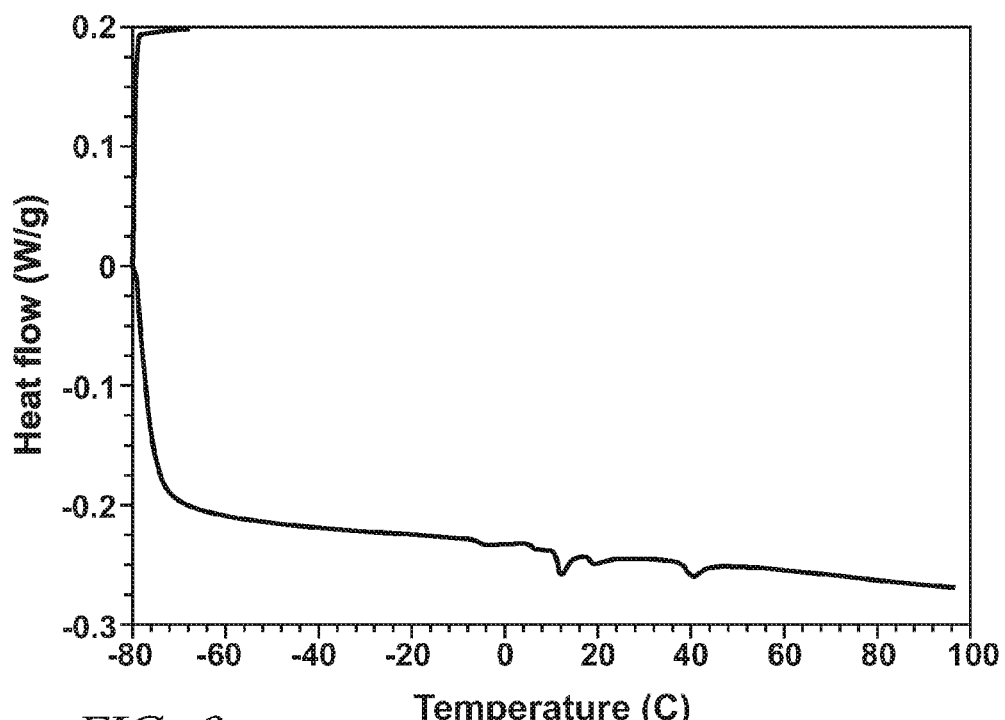
FIG. 9 is a plot of Heat Flow (W/g) vs. Temperature (° C.) and shows a thermogram for a 0.3M electrolyte solution of LiBFBDB in $PP_{13}^+/FSI^-$. Heat flow measurements were taken using DSC over the temperature range of −80 to +100° C. at a heating and cooling rate of 10° C. per minute.
Figure 13:
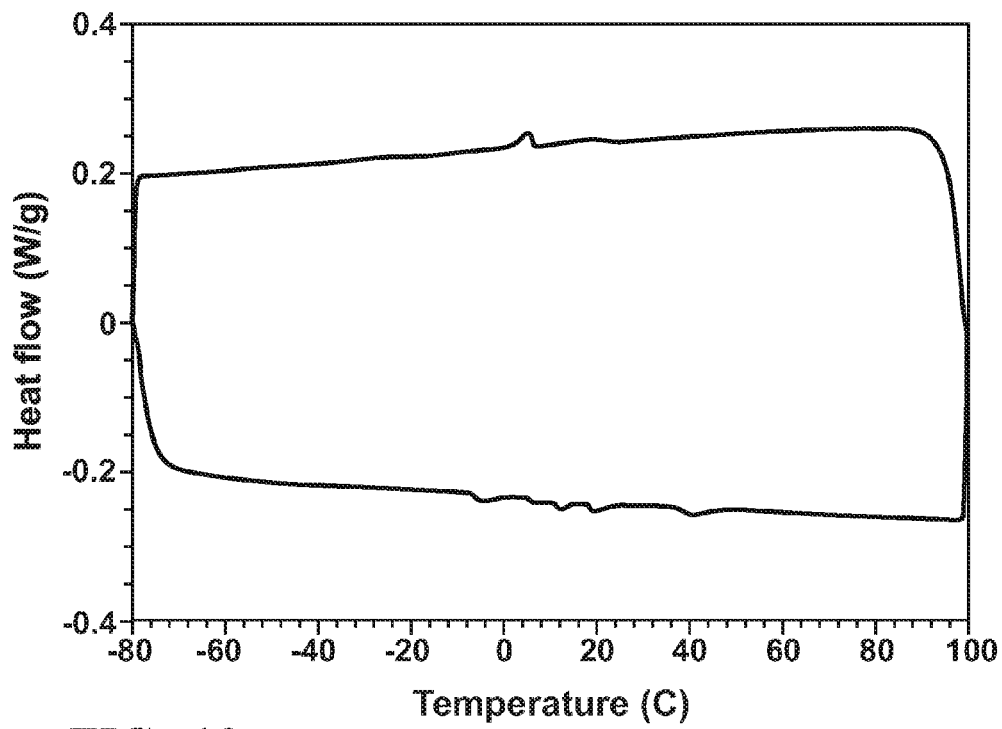
FIG. 13 is a plot of Heat Flow (W/g) vs. Temperature (° C.) and shows a thermogram for a 0.3M electrolyte solution of LiHFBTMB in $PP_{13}^+/FSI^-$ during a second heat and cool cycle. Heat flow measurements were taken using DSC over the temperature range of −80 to +100° C. at a heating and cooling rate of 10° C. per minute.

FIG. 4 shows the ionic conductivities of the as-synthesized 0.3M electrolyte solutions in a solvent of $PP_{13}^+$/FSI$^-$. In the upper temperature range, the ionic conductivities are comparable to those using $Py_{14}^+$/FSI$^-$ as the solvent. But, in the lower temperature range, the ionic conductivities are lower by an order of magnitude with almost no discernable phase transition. Corresponding thermograms, shown in FIG. 9 for 0.3M LiBFBDB and FIG. 13 for 0.3M LiHFBTMB are smooth, without any peaks or valleys, while the thermogram for 0.3M LiBHFPDB electrolyte solution is showing and endothermic peak at 3.4° C. with the corresponding exothermic peak at −13.96° C.

Figure 5:
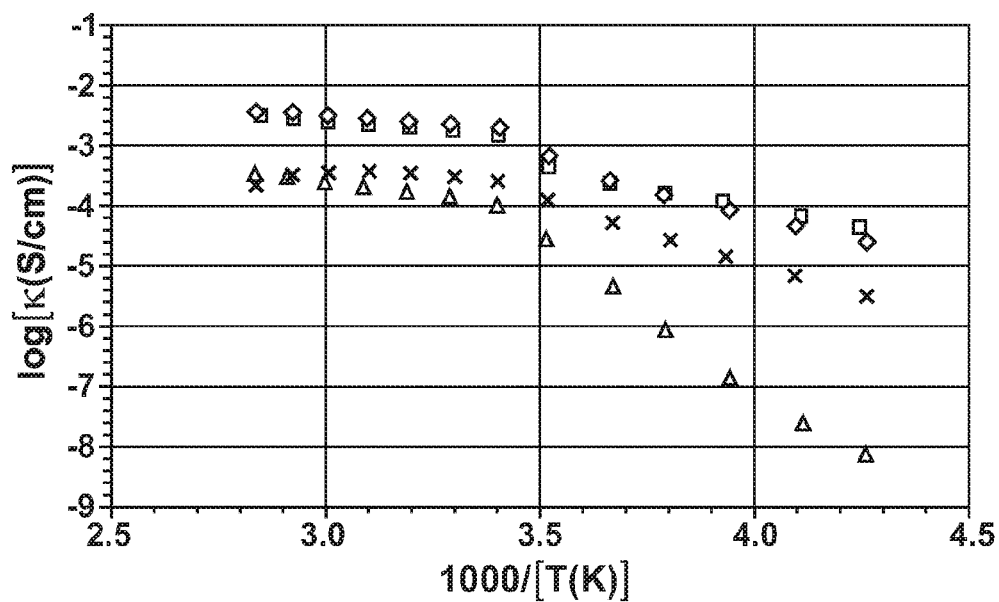
FIG. 5 is an Arrhenius plot of Ionic Conductivity (log [κ(S/cm)]) vs. 1000/T(K) and shows the ionic conductivity of four 0.3M electrolyte solutions over the temperature range of −40 to +80° C. Solid particles of the two new lithium salts and two known lithium salts were dissolved in a binary solvent of EC/DEC (1:1 v/v) to form the four 0.3M electrolyte solutions. Data points for 0.3M electrolyte solutions of LiBFBDB, LiBHFPDB, LiHFBTMB, and LiBOB are depicted as squares, Xs, diamonds, and triangles, respectively.

For comparison, FIG. 5 shows the ionic conductivities of the as-synthesized 0.3M electrolyte solutions in a mixture of organic carbonates (EC/DEC 1:1 v/v). The values corresponding to the LiBFBDB-containing electrolyte solution are comparable to those of the LiBOB electrolyte solution, but are slightly lower in the upper temperature range and are slightly higher in the lower temperature range. The values for the LiHFBTMB-containing electrolyte solution are one order of magnitude lower than the other two solutions in the upper temperature range and several orders of magnitude lower in the lower temperature range, while the values for LiBHFPDB-containing electrolyte solution are an order of magnitude lower over the entire temperature interval.

Figure 6:
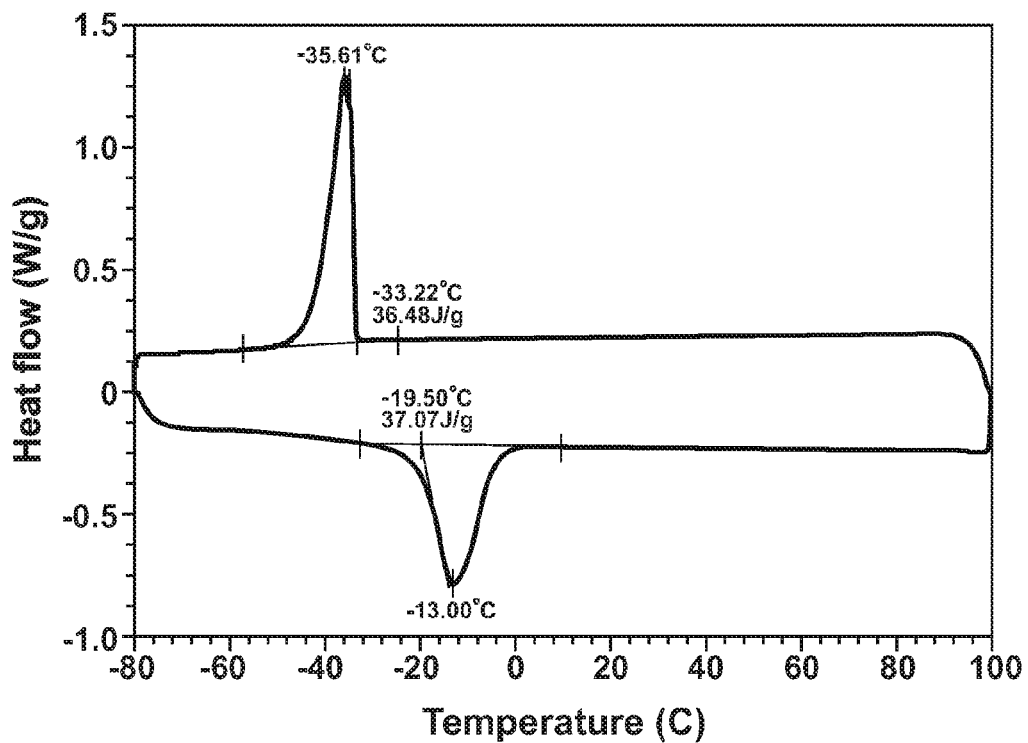
FIG. 6 is a plot of Heat Flow (W/g) vs. Temperature (° C.) and shows a thermogram for a 0.3M electrolyte solution of LiBFBDB in $EMIM^+/FSI^-$ during a second heat and cool cycle. Differential scanning calorimetry (DSC) was used to measure the thermal properties of the prepared electrolyte solution over the temperature range of −80 to +100° C. at a heating and cooling rate of 10° C. per minute.
Figure 10:
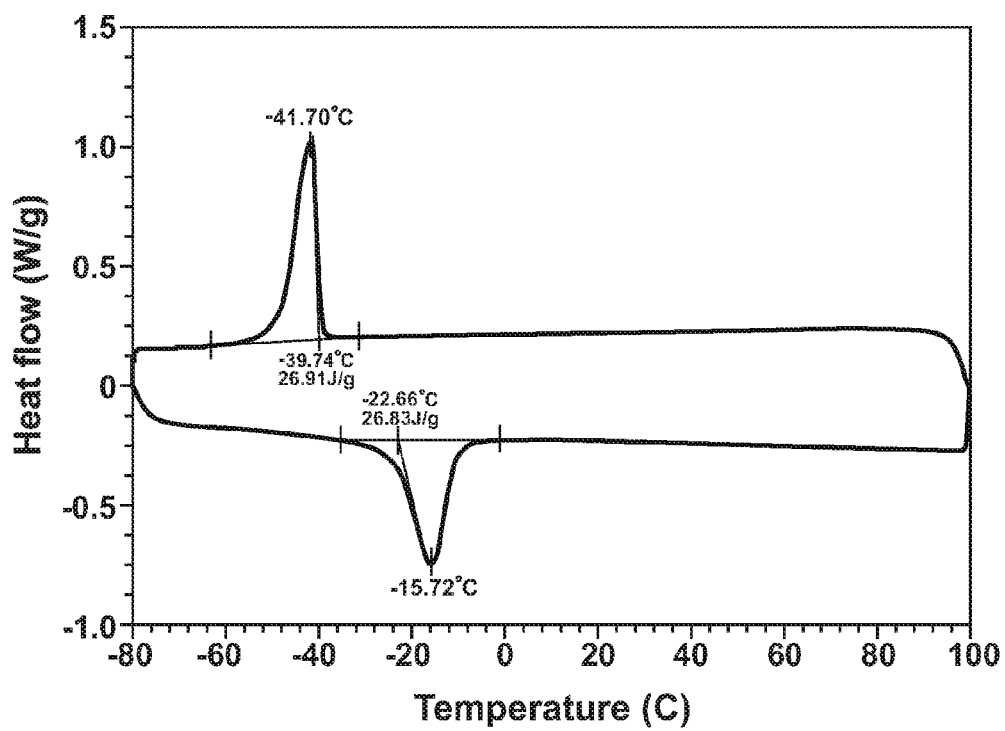
FIG. 10 is a plot of Heat Flow (W/g) vs. Temperature (° C.) and shows a thermogram for a 0.3M electrolyte solution of LiHFBTMB in $EMIM^+/FSI^-$ during a second heat and cool cycle. Heat flow measurements were taken using DSC over the temperature range of −80 to +100° C. at a heating and cooling rate of 10° C. per minute.
Figure 14:
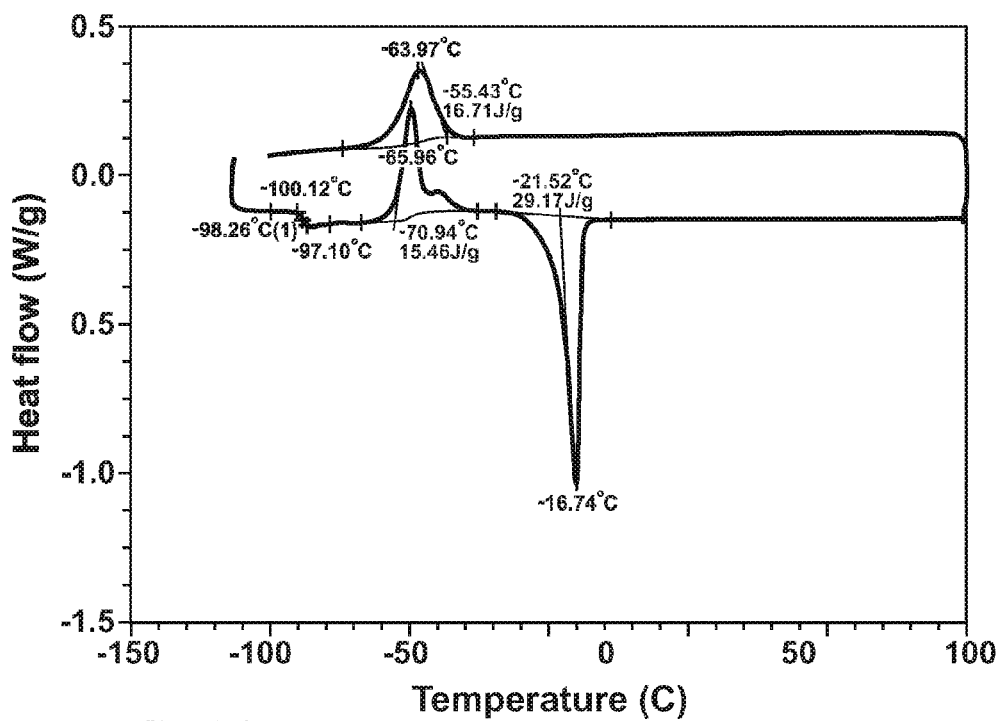
FIG. 14 is a plot of Heat Flow (W/g) vs. Temperature (° C.) and shows a thermogram for a 0.3M electrolyte solution of LiBHFPDB in EMIM$^+$/FSI$^-$ during a second heat and cool cycle. Heat flow measurements were taken using DSC over the temperature range of −120 to +100° C. at a heating and cooling rate of 10° C. per minute.

FIGS. 6, 10 and 14 are thermograms of 0.3 molar solutions of LiBFBDB, LiHFBTMB, and LiBHFPDB in a solvent of EMIM$^+$/FSI$^-$. FIG. 6 reveals that the 0.3M LiBFBDB solution goes through a phase transition at about −13° C., as evidenced by the corresponding endotherm. And FIG. 10 reveals that the 0.3M LiHFBTMB solution goes through a phase transition at about −15.7° C., while the 0.3M LiBHFPDB solution goes through a phase transition at about −16.7° C. These results support our conclusion that the abrupt drop in ionic conductivities of EMIM$^+$/FSI$^-$-based solutions at temperatures below −10° C. is likely due to freezing of the ionic liquid.

Figure 7:
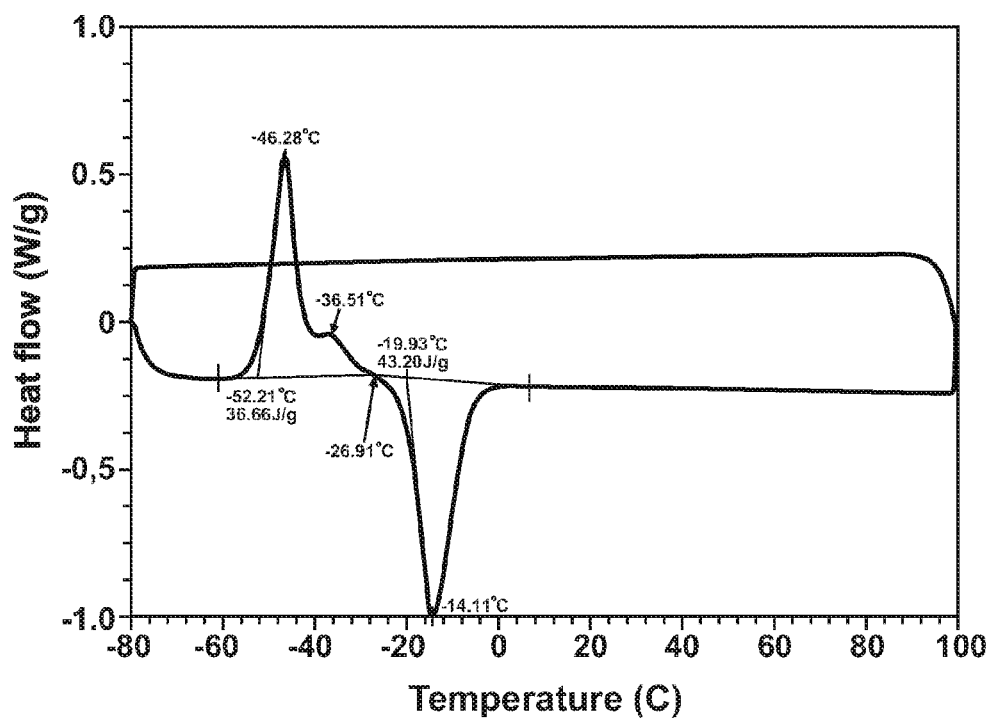
FIG. 7 is a plot of Heat Flow (W/g) vs. Temperature (° C.) and shows a thermogram for a 0.3M electrolyte solution of LiBFBDB in $EMIM^+/TFSI^-$ during a second heat and cool cycle. Heat flow measurements were taken using DSC over the temperature range of −80 to +100° C. at a heating and cooling rate of 10° C. per minute.
Figure 11:
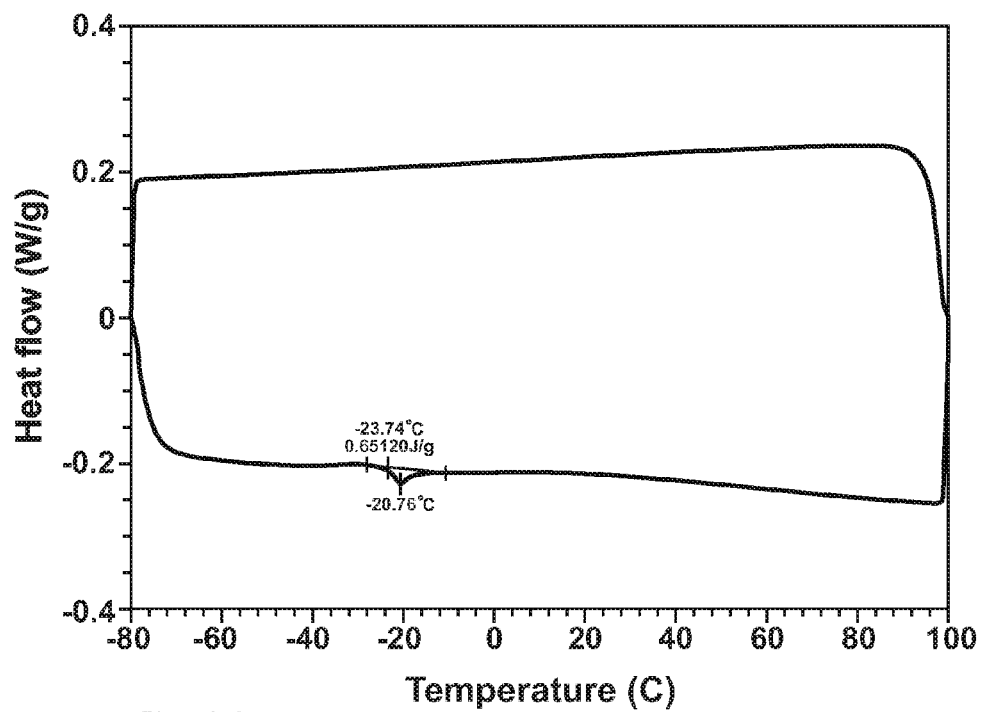
FIG. 11 is a plot of Heat Flow (W/g) vs. Temperature (° C.) and shows a thermogram for a 0.3M electrolyte solution of LiHFBTMB in $EMIM^+/TFSI^-$ during a second heat and cool cycle. Heat flow measurements were taken using DSC over the temperature range of −80 to +100° C. at a heating and cooling rate of 10° C. per minute.
Figure 15:
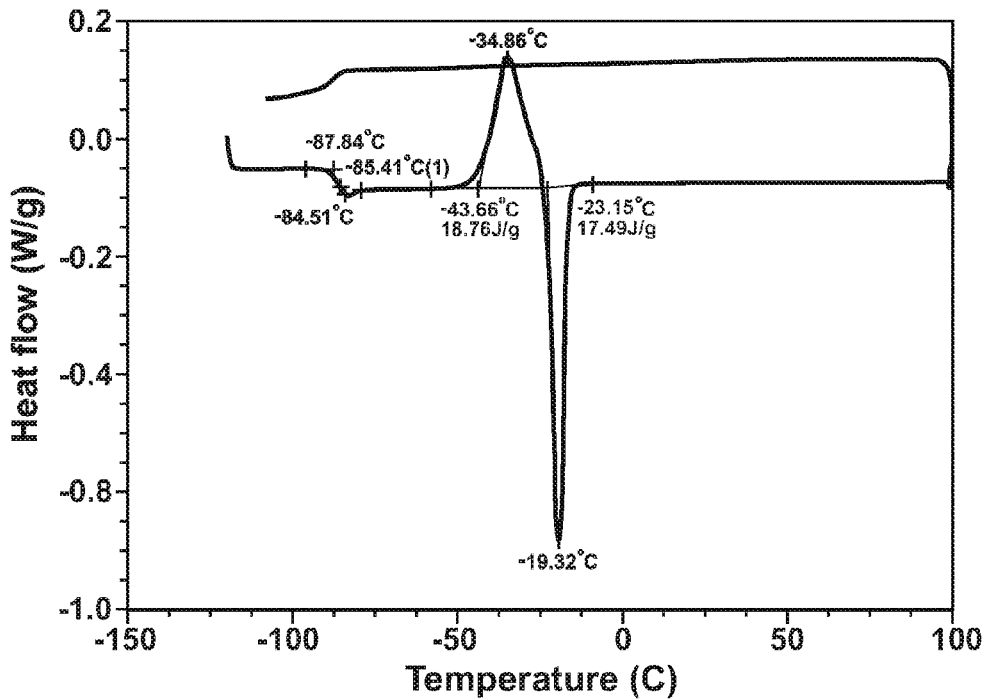
FIG. 15 is a plot of Heat Flow (W/g) vs. Temperature (° C.) and shows a thermogram for a 0.3M electrolyte solution of LiBHFPDB in EMIM$^+$/TFSI$^-$ during a second heat and cool cycle. Heat flow measurements were taken using DSC over the temperature range of −120 to +100° C. at a heating and cooling rate of 10° C. per minute.

FIGS. 7, 11 and 15 are thermograms of a 0.3M LiBFBDB, LiHFBTMB and LiBHFPDB electrolyte solutions using a solvent of EMIM$^+$/TFSI$^-$. FIG. 7 reveals that the 0.3M LiBFBDB solution goes through a phase transition at about −14.1° C., as evidenced by the corresponding endotherm. And FIG. 11 reveals that the 0.3M LiHFBTMB solution goes through a phase transition at about −20.8° C., while FIG. 15 reveals that the 0.3M LiBHFPDB solution goes through a steeper phase transition at about −19.3° C. These results support our conclusion that the abrupt drop in ionic conductivities of EMIM$^+$/TFSI$^-$-based solutions at temperatures below −10° C. is likely due to freezing of the ionic liquid.

Figure 18:
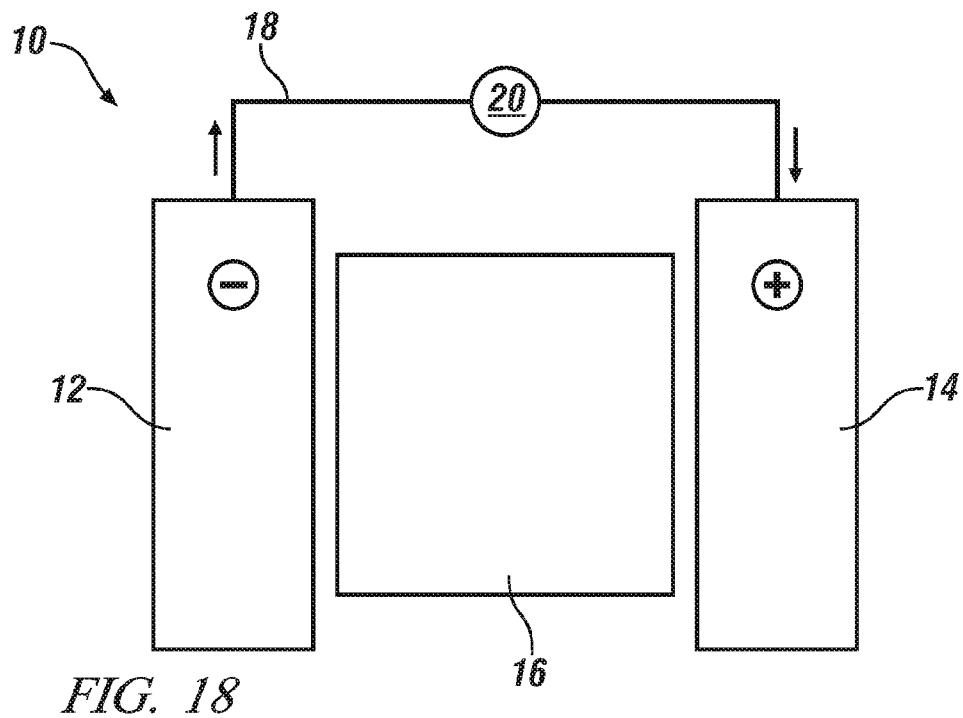
FIG. 18 is a schematic illustration of an embodiment of a single lithium-ion electrochemical cell having a negative electrode, a positive electrode, and an electrolyte.

Accordingly, the new lithium fluorinated orthoborate compounds are considered to have significant value in lithium-ion cells to increase the output and life of the cells. A schematic illustration of an arrangement of the electrodes and electrolyte is presented in FIG. 18. A single lithium-ion cell 10 is illustrated. The cell may be discharged and recharged. A lithium-ion battery typically comprises a plurality of cells, some of which are arranged in parallel electrical connection to deliver a specified power and some of which are connected in series to deliver a desired electrical potential.

A representative cell 10 comprises a negative electrode 12, a positive electrode 14, and an electrolyte 16. It will be recognized that the negative electrode 12 is the anode on cell discharge and the positive electrode 14 is the cathode. The negative electrode 12 may, for example, be formed of a thin flat layer of graphite flake particles that are resin bonded to a surface of a thin aluminum sheet which serves as a current collector. In the charged state of the cell the graphite particles are intercalated with lithium. The positive electrode 14 may, for example, be formed of a thin layer of particle of a nickel-manganese oxide composition that is susceptible to intercalation with lithium ions during discharge of the cell to form $LiNi_{0.5}Mn_{1.5}O_4$. A thin layer of the positive electrode material may be bonded to a surface of a thin sheet of copper which serves as a current collector. Typically the negative electrode 12 and positive electrode 14 are located in close face-to-face relationship but kept from direct electrical contact with a thin porous polymer separator (not illustrated in FIG. 18). A liquid electrolyte 16 contacts the facing surfaces of the negative electrode 12 and positive electrode 14. Electrolyte 16 may be composed, as described above, of $LiPF_6$ and a small amount of another lithium salt both dissolved, for example, in a mixture of ethyl carbonate and dimethyl carbonate solvent. This combination of electrode materials and connecting electrolyte provides an electrical potential of up to about 4.5 volts depending on the electrode compositions. Lithium ions are formed in the negative electrode 12 and electrons are released from the negative electrode and pass through an external circuit 18 and load 20 to the positive electrode 14. Lithium ions flow from the negative electrode 12, through electrolyte 16, and are received into the material of positive electrode 14.

The cell 10 is viewed as discharged when much of the lithium has been removed from the negative electrode 12 and transported through the electrolyte 16 into the material of the positive electrode 14. The cell 10 may be recharged by application of a suitable electrical potential between the electrodes to promote transport of lithium ions from the cathode material through the electrolyte back into the anode material.

The new lithium borate salts of this invention contribute to improved electrolyte and cell performance in lithium-ion cells and batteries.

Practices of this invention have been illustrated by a few examples that are not limiting of the scope of the invention.

The invention claimed is:
1. A lithium salt, comprising:
   a lithium cation; and
   a borate ester chelate complex with two bidentate ligands coordinated to a single boron atom to form two chelate rings, each chelate ring comprising two oxygen atoms bonded to said boron atom, one methylene group bonded to each of said oxygen atoms, and one or more fluorinated carbon atoms bonded to and forming a cyclic bridge between said methylene groups.

2. A lithium salt as recited in claim 1 wherein said bidentate ligands are diols.

3. A lithium salt as recited in claim 1 wherein said bidentate ligands are 2,2,3,3-tetrafluoro-1,4-butanediol or 2,2,3,3,4,4-hexafluoro-1,5-pentanediol.

4. An electrolyte solution for a lithium-ion battery, said electrolyte solution comprising:
   lithium cations; and
   borate ester anions, said anions having two bidentate ligands coordinated to a single boron atom to form two chelate rings, each chelate ring comprising two oxygen atoms bonded to said boron atom, one methylene group bonded to each of said oxygen atoms, and one or more fluorinated carbon atoms bonded to and forming a cyclic bridge between said methylene groups.

5. An electrolyte solution as recited in claim 4 wherein said bidentate ligands are diols.

6. An electrolyte solution as recited in claim 4 wherein said bidentate ligands are 2,2,3,3-tetrafluoro-1,4-butanediol or 2,2,3,3,4,4-hexafluoro-1,5-pentanediol.

7. An electrolyte solution as recited in claim 4 further comprising: a non-aqueous organic solvent or a non-aqueous ionic liquid.

8. The electrolyte solution of claim 4 wherein said electrolyte solution has an electrolyte concentration of less than one mole per liter.

9. A lithium-ion battery comprising:
a negative electrode;
a positive electrode; and
an electrolyte comprising a lithium borate salt with a borate ester anion, said anion having two bidentate ligands coordinated to a single boron atom to form two chelate rings, each chelate ring comprising two oxygen atoms bonded to said boron atom, one methylene group bonded to each of said oxygen atoms, and one or more fluorinated carbon atoms bonded to and forming a cyclic bridge between said methylene groups.

10. A lithium-ion battery as recited in claim 9 wherein said bidentate ligands are diols.

11. A lithium-ion battery as recited in claim 9 wherein said bidentate ligands are 2,2,3,3-tetrafluoro-1,4-butanediol or 2,2,3,3,4,4-hexafluoro-1,5-pentanediol.

12. A lithium-ion battery as recited in claim 9 wherein said electrolyte further comprises a non-aqueous organic solvent or a non-aqueous ionic liquid.

13. A lithium-ion battery as recited in claim 9 wherein said electrolyte has a concentration of less than one mole per liter.

* * * * *